United States Patent
Ahn

(10) Patent No.: US 9,095,304 B2
(45) Date of Patent: Aug. 4, 2015

(54) PORTABLE ULTRASONIC DIAGNOSTIC APPARATUS

(75) Inventor: Mi Jeoung Ahn, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

(21) Appl. No.: 13/541,520

(22) Filed: Jul. 3, 2012

(65) Prior Publication Data
US 2013/0012817 A1 Jan. 10, 2013

(30) Foreign Application Priority Data
Jul. 4, 2011 (KR) .................. 10-2011-0066162

(51) Int. Cl.
*A61B 8/14* (2006.01)
*A61B 8/13* (2006.01)
*A61B 8/00* (2006.01)

(52) U.S. Cl.
CPC .............. *A61B 8/4427* (2013.01); *A61B 8/462* (2013.01); *A61B 8/467* (2013.01)

(58) Field of Classification Search
CPC ....... A61B 8/4427; A61B 8/462; A61B 8/467
USPC ................... 600/437–447, 459–463; 382/128
See application file for complete search history.

(56) References Cited

U.S. PATENT DOCUMENTS

| | | | | |
|---|---|---|---|---|
| 5,543,588 | A * | 8/1996 | Bisset et al. | 178/18.06 |
| 5,572,237 | A * | 11/1996 | Crooks et al. | 345/156 |
| 7,212,399 | B2 * | 5/2007 | Kee et al. | 361/679.09 |
| 2004/0263484 | A1 * | 12/2004 | Mantysalo et al. | 345/173 |
| 2010/0145195 | A1 * | 6/2010 | Hyun | 600/437 |
| 2011/0242003 | A1 * | 10/2011 | Osann, Jr. | 345/173 |

FOREIGN PATENT DOCUMENTS

KR 2010-0065720 A 6/2010

OTHER PUBLICATIONS

Korean Office Action issued in Korean Patent Application No. 10-2011-0066162 dated Jul. 31, 2012.

* cited by examiner

*Primary Examiner* — Michael Rozanski
(74) *Attorney, Agent, or Firm* — McDermott Will & Emery LLP

(57) ABSTRACT

A portable ultrasonic diagnostic apparatus has an ultrasonic probe, and a main body including a display unit provided on a front surface of the main body. An input device is provided at a rear surface of the main body to receive user command information from a user, which allows the user to operate the portable ultrasonic diagnostic apparatus with a hand that is gripping the portable ultrasonic diagnostic apparatus. The apparatus may be used by moving the ultrasonic probe in contact with a surface of an object, sending ultrasonic signals from the object surface, receiving reflected ultrasonic signals from the object, and converting the ultrasonic signals into electrical signals.

15 Claims, 12 Drawing Sheets

PORTABLE ULTRASONIC DIAGNOSTIC APPARATUS

CROSS-REFERENCE TO RELATED APPLICATION

This application claims the benefit of Korean Patent Application No. 2011-0066162, filed on Jul. 4, 2011 in the Korean Intellectual Property Office, the disclosure of which is incorporated herein by reference.

BACKGROUND

1. Field

The present disclosure is directed to a portable, hand-held, ultrasonic diagnostic apparatus, provided with an input device to allow a user to grip and operate the apparatus with one hand.

2. Description of the Related Art

Ultrasonic diagnostic apparatuses direct ultrasonic signals from a body surface of an object to a desired region inside a human body, and obtain an image related to a mono layer of a soft tissue or a blood stream using the ultrasonic signals reflected from the object, i.e. information of the ultrasonic echo signals in a non-invasive manner. Such ultrasonic diagnostic apparatuses have a smaller size, lower price, functionality of real-time display and higher safety by elimination of X-ray exposure, as compared to other imaging diagnostic apparatuses, such as X-ray diagnostic systems, Computerized Tomography (CT) scanners, Magnetic Resonance Imaging (MRI) equipment, nuclear medicine diagnostic apparatuses, and the like. Accordingly, ultrasonic diagnostic apparatuses have been widely used for cardiac, abdominal, urinary and gynecologic diagnosis.

Most ultrasonic diagnostic apparatuses are bulky and heavy and thus, have been fixedly installed at particular locations. Even in the case of small ultrasonic diagnostic apparatuses, they typically have a weight of 10 kg or more and thus, are not easy to move and are not portable. However, emergency rooms, operating rooms and other optional places for ultrasonic diagnosis may need small ultrasonic diagnostic apparatuses that are easily movable. For this reason, portable ultrasonic diagnostic apparatuses have been developed to overcome disadvantages of ultrasonic diagnostic apparatuses as described above.

Although use of such a portable ultrasonic diagnostic apparatus is increasing because it advantageously has a minimized size or weight and is easily carried, placing the portable ultrasonic diagnostic apparatus at a fixed position may be essential to allow a user to operate the portable ultrasonic diagnostic apparatus with one hand because the other hand of the user may be required to grip an ultrasonic probe so as to scan an object. To this end, a platform, cart or the like, on which the portable ultrasonic diagnostic apparatus is placed, may be additionally provided, and the portable ultrasonic diagnostic apparatus does not allow the user to grip and operate the portable ultrasonic diagnostic apparatus with one hand.

SUMMARY

It is an aspect of the present disclosure to provide a portable ultrasonic diagnostic apparatus in which an input device is provided at a rear surface of a main body, which allows a user to grip and operate the apparatus with one hand.

Additional aspects of the disclosure will be set forth in part in the description which follows and, in part, will be obvious from the description, or may be learned by practice of the disclosure.

In accordance with one aspect of the disclosure, a portable ultrasonic diagnostic apparatus having an ultrasonic probe includes a main body, and an input device provided at a rear surface of the main body to receive user command information from a user.

The main body may include a beam former to produce frame data by focusing ultrasonic signals received from the ultrasonic probe, an ultrasonic data producer to produce ultrasonic data via digital signal processing of the frame data, an ultrasonic image producer to produce an ultrasonic image using the ultrasonic data, and a controller to control display of the ultrasonic image and a user interface according to the user command information.

The controller may control provision of the user interface and optimization of the ultrasonic image according to the user command information.

The input device may include a track ball.

The track ball may input the user command information corresponding to a request and selection of the user interface.

The track ball may input the user command information corresponding to a setting request of a region of interest included in the ultrasonic image, a size adjusting request of the region of interest, and a movement request of the region of interest.

The input device may include at least one button provided at upper and lower sides or left and right sides of the track ball.

The at least one button may include a first button to change a display mode of the ultrasonic image or a second button to pause a display screen of the ultrasonic image.

The input device may include an image mode change button to change an ultrasonic image mode.

The input device may include a touch panel.

The input device may be separably coupled to the main body.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
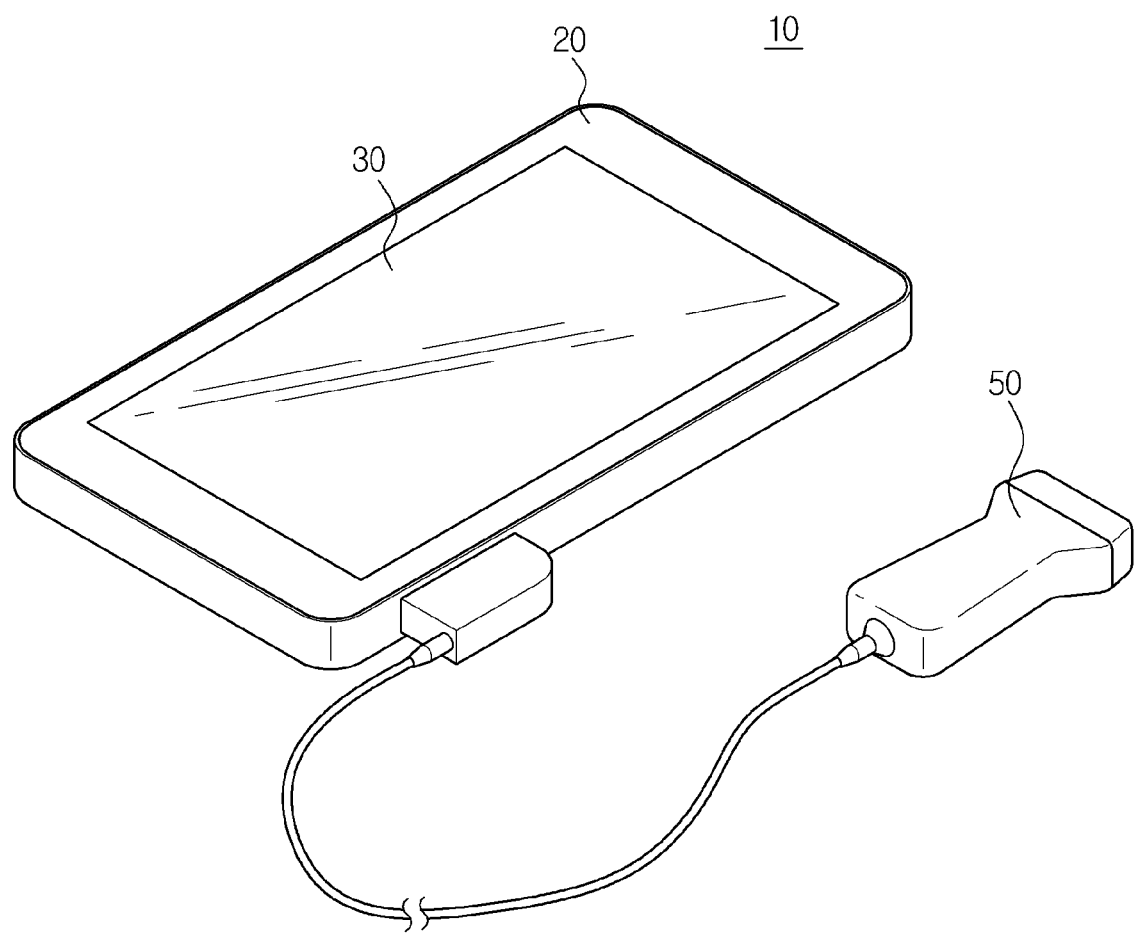
FIG. 1 is a front perspective view illustrating a configuration of a portable ultrasonic diagnostic apparatus according to an embodiment of the present disclosure.

Reference will now be made in detail to various embodiments of the present disclosure, examples of which are illustrated in the accompanying drawings, wherein like reference numerals refer to like elements throughout.

Figure 2:
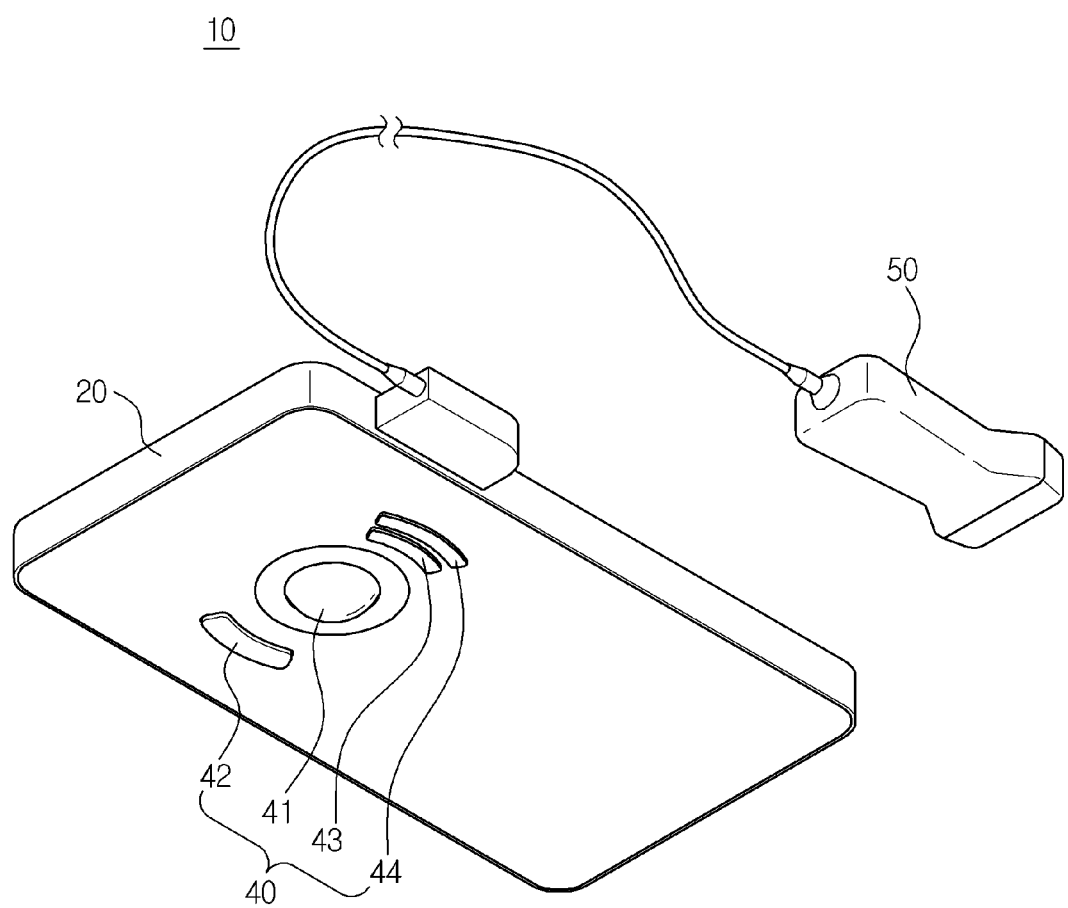
FIG. 2 is a rear perspective view of the portable ultrasonic diagnostic apparatus of FIG. 1.

FIG. 1 is a front perspective view illustrating a configuration of a portable ultrasonic diagnostic apparatus according to an embodiment of the present disclosure, and FIG. 2 is a rear perspective view of the portable ultrasonic diagnostic apparatus of FIG. 1.

As shown in FIGS. 1 and 2, the portable ultrasonic diagnostic apparatus 10 includes a main body 20, a display unit 30, and an input device 40. The main body 20 generally has a rectangular shape and defines an external appearance of the apparatus. The display unit 30 is installed to a front surface of the main body 20 and serves to display ultrasonic images related to various diagnostic information of the portable ultrasonic diagnostic apparatus 10. The input device 40 is installed to a rear surface of the main body 20 and serves to receive various operating commands of the portable ultrasonic diagnostic apparatus 10 from a user.

The portable ultrasonic diagnostic apparatus 10 further includes an ultrasonic probe 50 having a transducer element, which sends ultrasonic signals to an object (e.g., a body region, such as the liver, the kidneys, the pancreas, the heart, etc.) and receives the ultrasonic signals reflected from the object (i.e. ultrasonic echo signals) to convert the ultrasonic signals to electrical signals. The ultrasonic probe 50 may be connected to the main body 20 in a wired or wireless manner.

The main body 20 has a size and weight (e.g., 1 kg or less) to allow a user to grip the main body 20 with one hand. The main body 20 receives ultrasonic signals from the ultrasonic probe 50 and forms 2-Dimensional (2D) or 3-Dimensional (3D) ultrasonic images using the received ultrasonic signals.

The main body 20 is operated upon receiving electric power required to drive the portable ultrasonic diagnostic apparatus 10 from an integrated battery or an external power source.

The main body 20 includes a connection unit connected to a connector provided at one end of the ultrasonic probe 50 and sends and receives signals to or from the ultrasonic probe 50 through the connection unit.

The display unit 30 is constructed of light emitting elements, such as Light Emitting Diodes (LEDs), a Liquid Crystal Display (LCD), Organic Light Emitting Diodes (OLEDs), and the like. The display unit 30 displays 2D or 3D ultrasonic images produced in the main body 20.

The display unit 30 receives a user command corresponding to a request, selection and the like of a user interface from the input device 40, and produces and displays user input information corresponding to the input user command.

The display unit 30 displays ultrasonic images upon receiving a user command corresponding to a setting request, a size adjusting request, a movement request, and the like related to a region of interest. The display unit 30 displays the ultrasonic images along with names and setting values of set parameters.

The input device 40 receives a user command related to operation of the portable ultrasonic diagnostic apparatus 10. The input device 40 may include a track ball, buttons or key switches, a sliding resistor, a rotary encoder, and the like.

The input device 40 is provided at the rear surface of the main body 20 to allow the user to operate the main body 20 with a hand that is gripping the main body 20. Those skilled in the art will appreciate that the input device 40 provided at the rear surface of the main body 20 may be installed at optional positions so long as it is operable by the user hand that is gripping the main body 20.

In the embodiment of the present disclosure, the input device 40 includes a track ball 41 having high operation freedom and one or more buttons 42 and 43 provided at upper and lower sides of the track ball 41, thereby providing a User Interface (UI).

The track ball 41 inputs a user command corresponding to a request, selection and the like of a user interface and also, inputs a user command corresponding to a setting request, size adjusting request, movement request, and the like related to a region of interest included in a displayed ultrasonic image.

The one or more buttons 42 and 43 include a first button 42 to change a display mode of an ultrasonic image and a second button 43 to pause a display screen of the ultrasonic image.

The first button 42 is a display mode change button to change a display mode of an ultrasonic image to be displayed on the display unit 30. In other words, an ultrasonic image mode to be displayed on the display unit 30, such as a Brightness (B) mode, a Color (C) mode, a Pulsed-Wave (PW) mode, Motion (M) mode, Doppler (D) mode, Continuous Wave (CW) mode, and the like, is changed by pushing the first button 42.

The second button 43 is a freeze button to pause a display screen of an ultrasonic image to enable observation of an ultrasonic image displayed on the display unit 30. In other words, a screen of an ultrasonic image that is being displayed on the display unit 30 is paused by pushing the second button 43.

Although the present embodiment describes the first button 42 and the second button 43 as being arranged at upper and lower sides of the track ball 41 to allow the user to operate the same with one hand, the disclosure is not limited thereto and the first button 42 and the second button 43 may be arranged at left and right sides of the track ball 41 so long as they are operable using one hand.

In other embodiments, the first and second buttons 42 and 43 may be arranged in parallel at any one side of the upper and lower sides or of the left and right sides of the track ball 41. Those who skilled in the art will appreciate that arrangements of the first button 42 and the second button 43 may be freely selected so long as the user can operate the input device 40 provided at the rear surface of the main body 20 with one hand that is gripping the main body 20.

In addition, although the embodiment of the present disclosure describes the first button 42 as a display mode change button and the second button 43 as a freeze button by way of example, the disclosure is not limited thereto and functions of the first button 42 and the second button 43 may be exchanged. As necessary, additional buttons other than the first and second buttons 42 and 43 may be provided, or the track ball 41 may perform functions of the first button 42 and the second button 43. For example, a freeze function of the second button may be realized by pushing the track ball, which enables omission of at least one of the first button 42 and the second button 43.

In one embodiment of the present disclosure, the input device 40 may include an image mode change button 44 to change an ultrasonic image mode. The image mode change button 44 is a button to change a mode of an ultrasonic image that is being displayed on the display unit 30. For example, the mode may include a gain, edge reinforcement, power, and the like, of the ultrasonic image.

Although the embodiment of the present disclosure describes the image mode change button 44 as being arranged along with the track ball 44 by way of example, the disclosure is not limited thereto and the image mode change button 44 may be provided alone without the track ball 41 to receive a user command related to operation of the portable ultrasonic diagnostic apparatus 10.

The portable ultrasonic diagnostic apparatus 10 may be implemented using a mobile device, for example, a mobile phone.

Figure 3A:
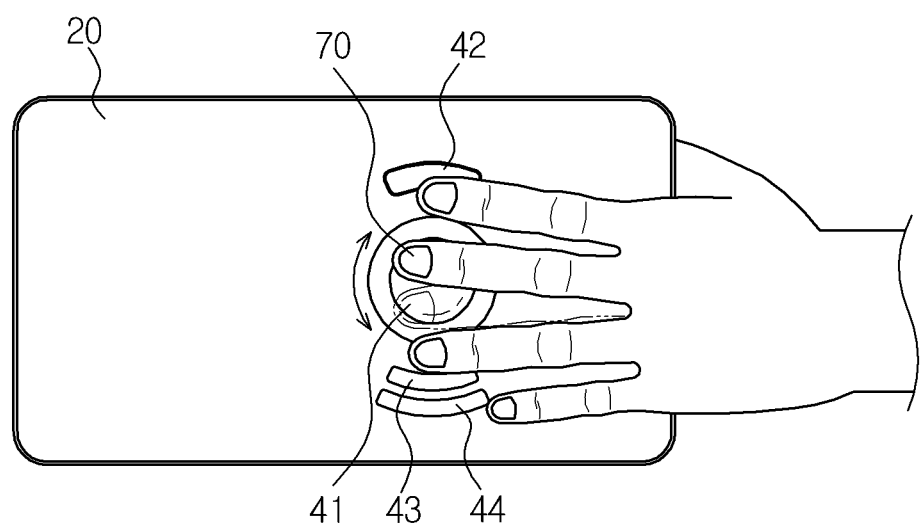
FIGS. 3A to 3C are views illustrating user command input methods according to embodiments of the present disclosure.
Figure 3B:
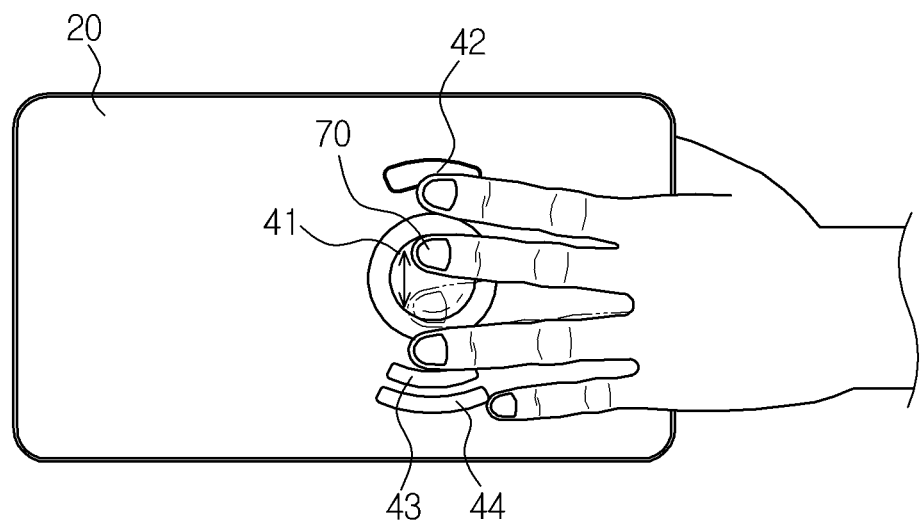
Figure 3C:
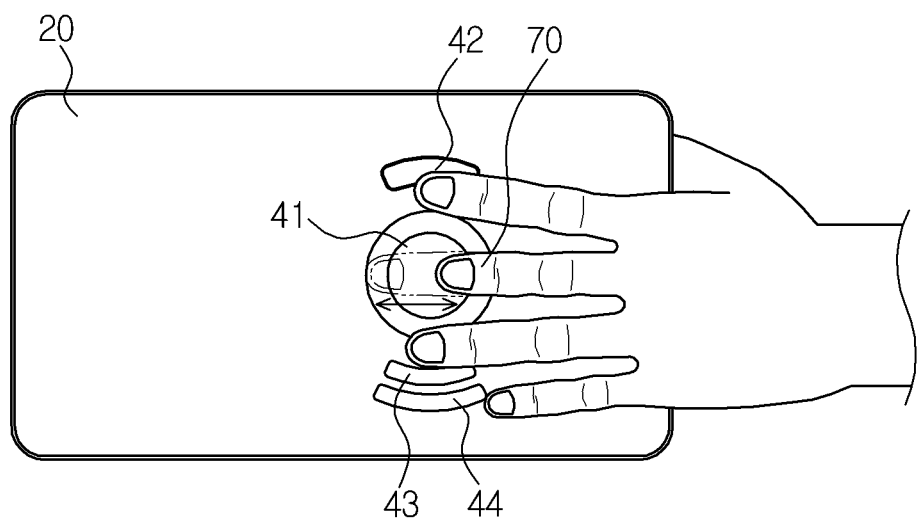

Hereinafter, a user command input method using the track ball 41 will be described with reference to FIGS. 3A to 3C. FIGS. 3A to 3C are views illustrating user command input methods according to embodiments of the present disclosure.

User command input methods using the track ball 41 may include a method of pushing and releasing the track ball 41 (hereinafter, referred to as a click method), a method of scrolling the track ball 41 in a circular direction while pushing the track ball 41 with a finger 70 as illustrated in FIG. 3A (hereinafter, referred to as a touch and circular scroll method), a method of scrolling the track ball 41 in a vertical direction while pushing the track ball 41 with the finger 70 as illustrated in FIG. 3B (hereinafter, referred to as a touch and vertical scroll method), and a method of scrolling the track ball 41 in a horizontal direction while pushing the track ball 41 with the finger 70 as illustrated in FIG. 3C (hereinafter, referred to as a touch and horizontal scroll method). Operations to provide a user interface using the track ball 41 will be described below in detail with reference to FIG. 6.

Figure 4:
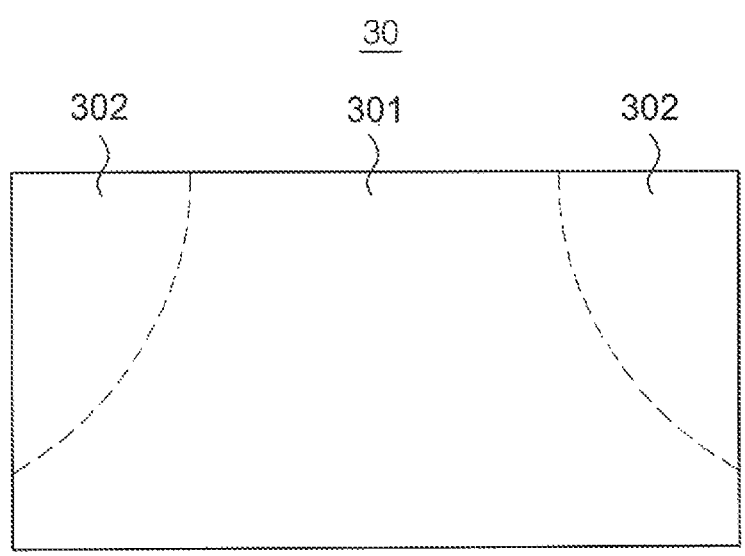
FIG. 4 is a view illustrating a display area of a display unit according to an embodiment of the present disclosure.

Hereinafter, a display area of the display unit 30 will be described with reference to FIG. 4. FIG. 4 is a view illustrating a display area of a display unit according to an embodiment of the present disclosure.

In the embodiment of the present disclosure, the display unit 30 includes a first area 31, which displays an ultrasonic image upon receiving a user command corresponding to a setting request, size adjusting request, movement request, and the like related to a region of interest, and a second area 32 which displays a user interface upon receiving a user command corresponding to a request, selection and the like of a user interface.

Accordingly, the user may observe desired diagnostic information while seeing an ultrasonic image displayed via the first area 31 and may select or change a menu of an ultrasonic image while seeing a user interface displayed via the second area 32.

Figure 5:
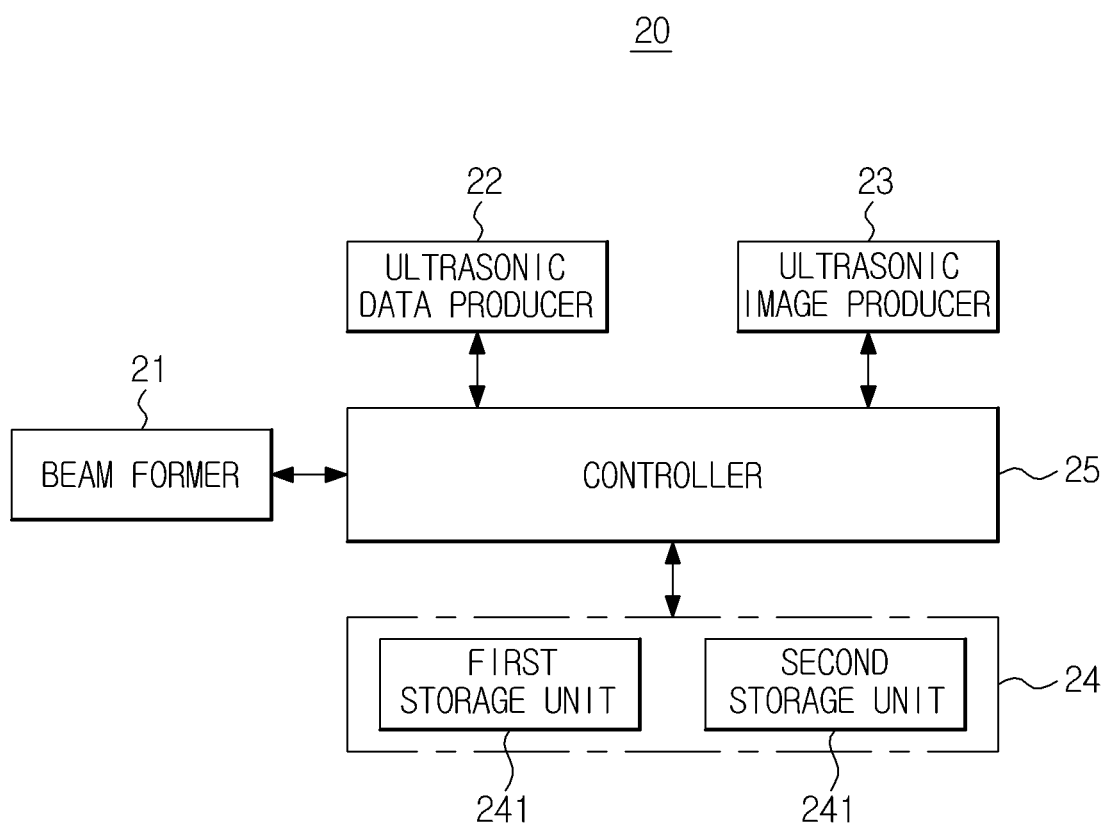
FIG. 5 is a block diagram of a configuration of a main body according to an embodiment of the present disclosure.

FIG. 5 is a block diagram of a configuration of the main body according to an embodiment of the present disclosure. In FIG. 5, the main body 20 includes a beam former 21, an ultrasonic data producer 22, an ultrasonic image producer 23, a storage unit 24 and a controller 25.

The beam former 21 focuses ultrasonic signals received from the ultrasonic probe 50 to produce frame data. The ultrasonic data producer 22 produces ultrasonic data via digital signal processing of the frame data input from the beam former 21. Thus, the ultrasonic data producer 22 may serve as a Digital Signal Processor (DSP).

The ultrasonic image producer 23 produces an ultrasonic image using the ultrasonic data. The ultrasonic image includes at least one of a Brightness (B) mode image, Color (C) mode image, Pulsed-Wave (PW) mode image, Motion (M) mode image, Doppler (D) mode image and Continuous Wave (CW) mode image.

The storage unit 24 stores the ultrasonic data produced by the ultrasonic data producer 22 on a per frame basis. Further, the storage unit 24 stores the ultrasonic image produced by the ultrasonic image producer 23. In one embodiment of the present disclosure, the storage unit 24 includes a first storage unit 241 to store the ultrasonic data on a per frame basis and a second storage unit 242 to store the ultrasonic image.

The controller 25 controls transmission/reception of ultrasonic signals and production/storage of ultrasonic data and ultrasonic images.

Further, the controller 25 controls display of an ultrasonic image. The controller 25 performs provision of a user interface and optimization of an ultrasonic image in response to a user command input via the input device 40. Hereinafter, operation of the controller 25 with regard to provision of a user interface will be described in detail.

Figure 6:
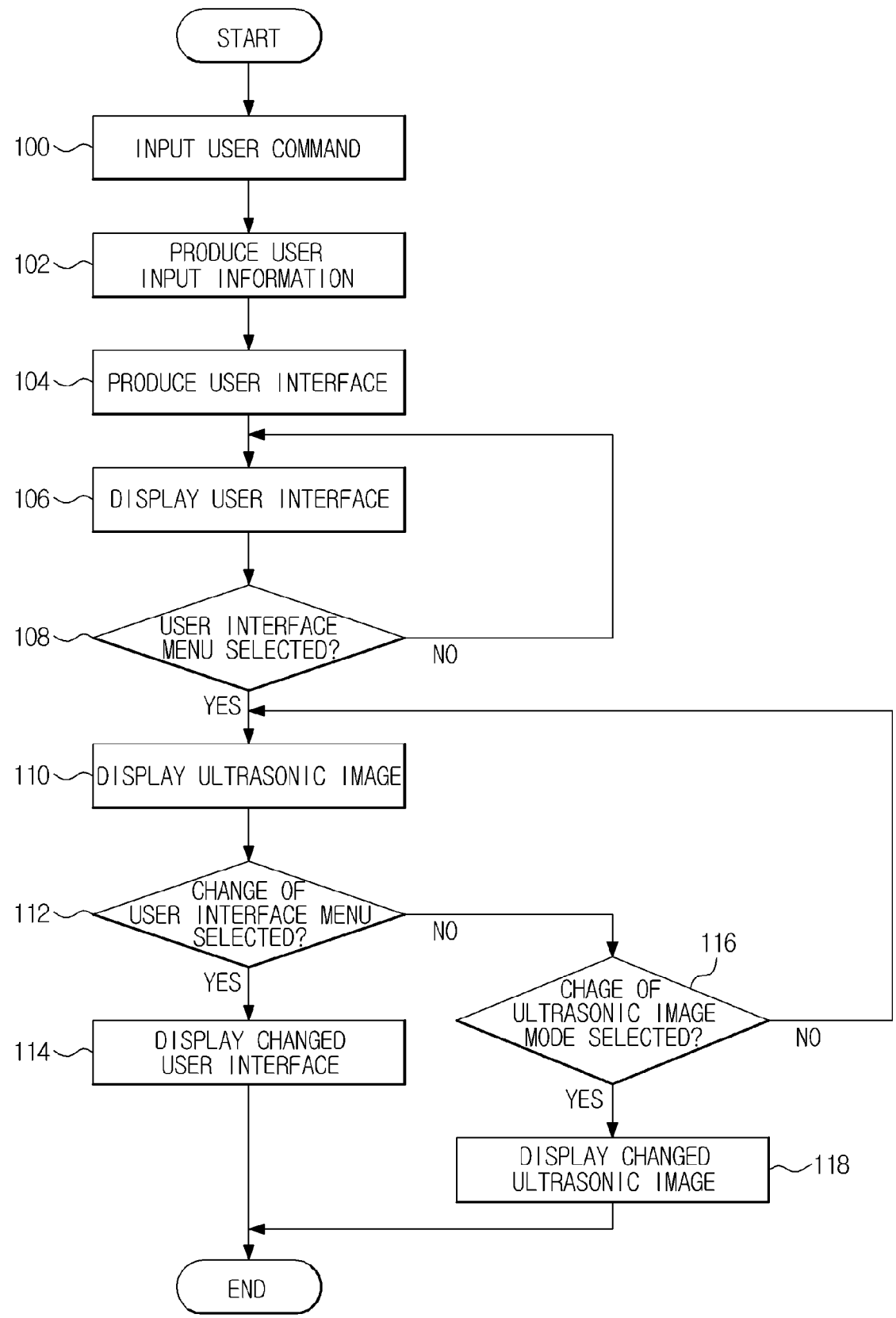
FIG. 6 is a flowchart illustrating an operating method of a controller which provides the portable ultrasonic diagnostic apparatus with a user interface according to an embodiment of the present disclosure.

FIG. 6 is a flowchart illustrating an operating method of the controller which provides the portable ultrasonic diagnostic apparatus with a user interface according to an embodiment of the present disclosure. In FIG. 6, the user grips the main body 20 of the portable ultrasonic diagnostic apparatus 10 with one hand and operates the input device 40 provided at the rear surface of the main body 20 using the hand that is gripping the main body 20.

If a user command to display an ultrasonic image is input by the user (100), the input device 40 produces user input information corresponding to the input user command and transmits the produced user input information to the controller 25 of the main body 20 (102).

If the user input information is transmitted from the input device 40, the controller 25 produces a user interface according to the transmitted user input information (104). In this case, the user interface may display selectable menu items and other menus depending on a user request.

The user interface may be changed in various ways according to a diagnostic mode with regard to production of an ultrasonic image as well as user convenience.

Next, the controller 25 controls display of the produced user interface and the user interface is displayed on the second area 32 of the display unit 30 under control of the controller 25 (106).

The user selects or changes a menu of the user interface using the track ball 41 of the input device 40 while seeing the user interface displayed on the second area 32 of the display unit 30.

If the menu of the user interface is selected, menu information of the selected user interface is transmitted to the controller 25.

Thus, if the menu information of the user interface is transmitted from the input device 40, the controller 25 controls production of an ultrasonic image to be displayed according to the menu information of the transmitted user interface.

A method of producing an ultrasonic image is as follows.

First, if the ultrasonic probe 50 is moved in contact with the body surface of an object to be diagnosed, the ultrasonic probe 50 sends ultrasonic signals from the body surface of the object to a desired region in the human body and receives the ultrasonic signals reflected from the object, i.e. ultrasonic echo signals to convert the ultrasonic signals into electrical signals.

The ultrasonic signals converted into the electrical signals by the ultrasonic probe 50 are transmitted to the main body 20 through the connection unit.

The beam former 21 of the main body 20 focuses the ultrasonic signals received from the ultrasonic probe 50 to produce frame data and transmits the produced frame data to the ultrasonic data producer 22.

The ultrasonic data producer 22 performs digital signal processing of the frame data input from the beam former 21 to produce ultrasonic data and the ultrasonic image producer 23 produces an ultrasonic image using the ultrasonic data. The ultrasonic image includes at least one of a Brightness (B) mode image, Color (C) mode image, Pulsed-Wave (PW) mode image, Motion (M) mode image, Doppler (D) mode image and Continuous Wave (CW) mode image.

In this case, the storage unit 24 stores the ultrasonic data produced by the ultrasonic data producer 22 on a per frame basis in the first storage unit 241, and stores the ultrasonic image produced by the ultrasonic image producer 23 in the second storage unit 242.

Thereby, the controller 25 controls display of the ultrasonic data and ultrasonic image stored in the first storage unit 241 and the second storage unit 242 in response to the user command via the input device 40. The ultrasonic image is displayed on the first area 31 of the display unit 30 under control of the controller 25.

Thereafter, when it is desired to change a menu of the user interface displayed on the first area 31 of the display unit 30, the user operates the track ball 41 provided at the rear surface of the main body 20 with one hand that is gripping the main body 20.

If a user command to change the menu of the user interface is input by the user (112), the input device 40 produces user change information corresponding to the input user command and transmits the produced user change information to the controller 25 of the main body 20.

If the user change information is transmitted from the input device 40, the controller 25 produces a user interface changed according to the transmitted user change information and displays the changed user interface on the second region 32 of the display unit 30 (114).

When it is desired to change a display mode of the ultrasonic image on the second area 32 of the display unit 30, the user operates the first button 42 provided at the rear surface of the main body 20 with one hand that is gripping the main body 20.

If a user command to change an ultrasonic image mode is input by the user (116), the input device 40 produces user change information corresponding to the input user command and transmits the produced user change information to the controller 25 of the main body 20.

If the user change information is transmitted from the input device 40, the controller 25 produces the ultrasonic image mode changed according to the transmitted user change information and displays an ultrasonic image of the changed mode on the first region 31 of the display unit 30 (118).

Although the embodiment of the present disclosure has described the input device 40 provided at the rear surface of the main body 20 as including the track ball 41 and the buttons 42, 43 and 44 by way of example, the disclosure is not limited thereto and the same effects as the disclosure may naturally be obtained even if the input device 40 includes a key switch, sliding resistor, rotary encoder, touch input device, and the like.

Figure 7:
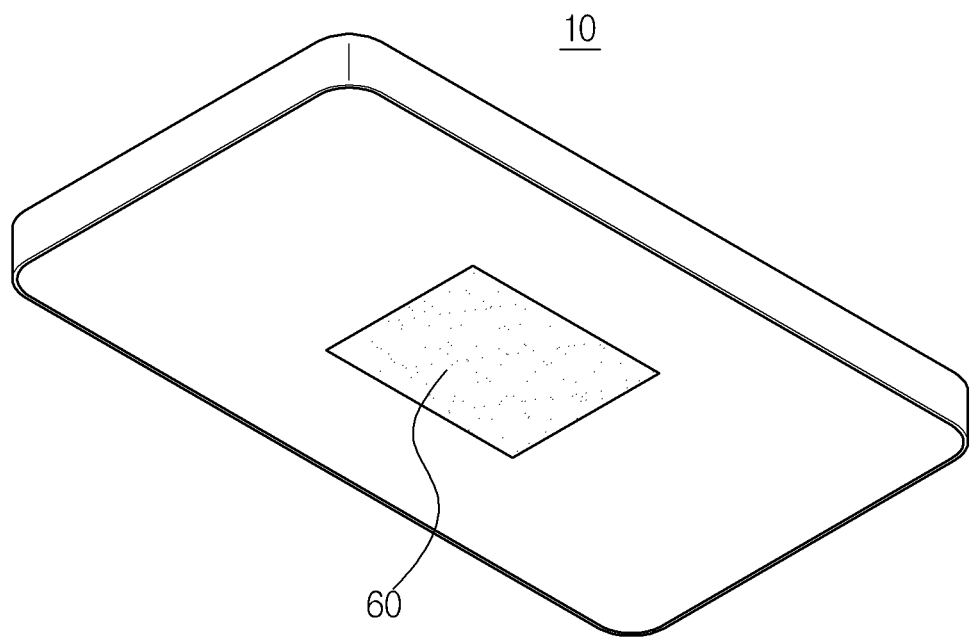
FIG. 7 is a rear perspective view illustrating a configuration of a portable ultrasonic diagnostic apparatus according to another embodiment of the present disclosure.

FIG. 7 is a rear perspective view illustrating a configuration of a portable ultrasonic diagnostic apparatus according to another embodiment of the present disclosure.

In FIG. 7, the portable ultrasonic diagnostic apparatus 10 is constructed such that a touch panel 60 is attached to the rear surface of the main body 20. The touch panel 60 is another example of the input device 40 that receives a user command related to operation of the portable ultrasonic diagnostic apparatus 10.

In one example, the touch panel 60 may select user command information, such as mode change, content change, screen pause, and the like for an ultrasonic image to be displayed on the display unit 30.

Figure 8:
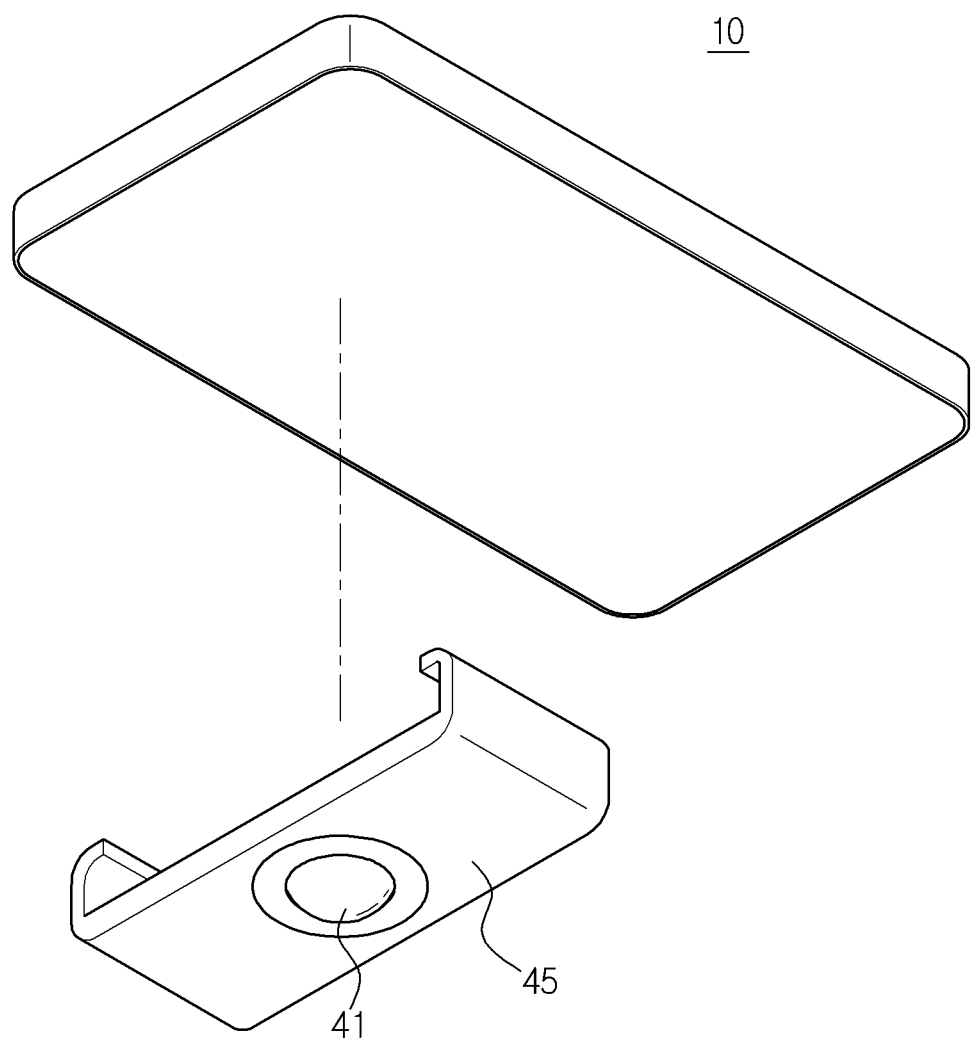
FIG. 8 is a rear perspective view illustrating a configuration of a portable ultrasonic diagnostic apparatus according to another embodiment of the present disclosure.
Figure 9:
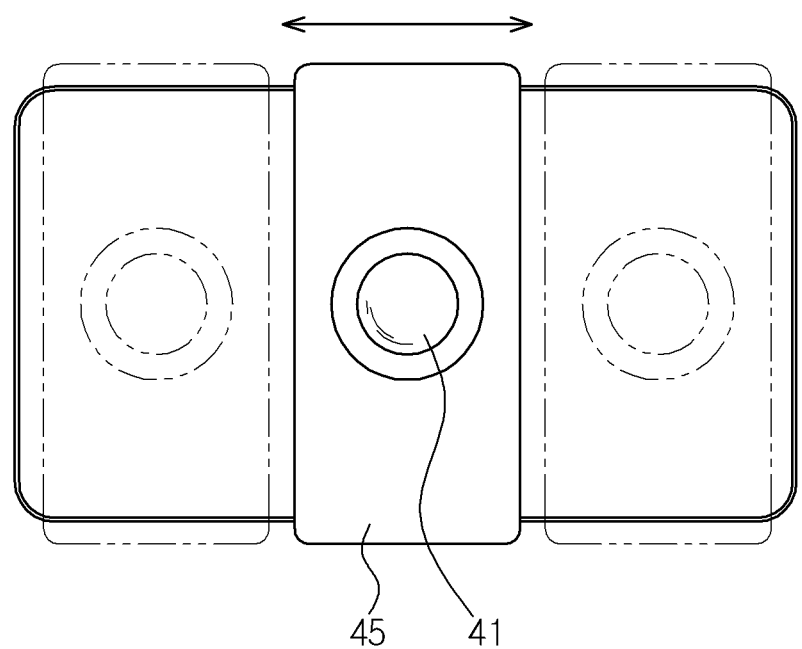
FIG. 9 is a view illustrating position change of a track ball with regard to the configuration of FIG. 8.

FIG. 8 is a rear perspective view illustrating a configuration of a portable ultrasonic diagnostic apparatus according to another embodiment of the present disclosure, and FIG. 9 is a view illustrating position change of a track ball with regard to the configuration of FIG. 8.

In FIGS. 8 and 9, the portable ultrasonic diagnostic apparatus 10 is configured such that a separable member 45 provided with the track ball 41 is mounted to the rear surface of the main body 10. The separable member 45 allows the user to freely change a position of the track ball 41 provided at the rear surface of the main body 20 in consideration of different sizes of user hands.

Accordingly, by coupling the separable member 45 provided with the track ball 41 to a desired position of the rear surface of the main body 20, the user can operate the track ball 41 while gripping the main body 20 with one hand regardless of the size of the user's hand.

Figure 10:
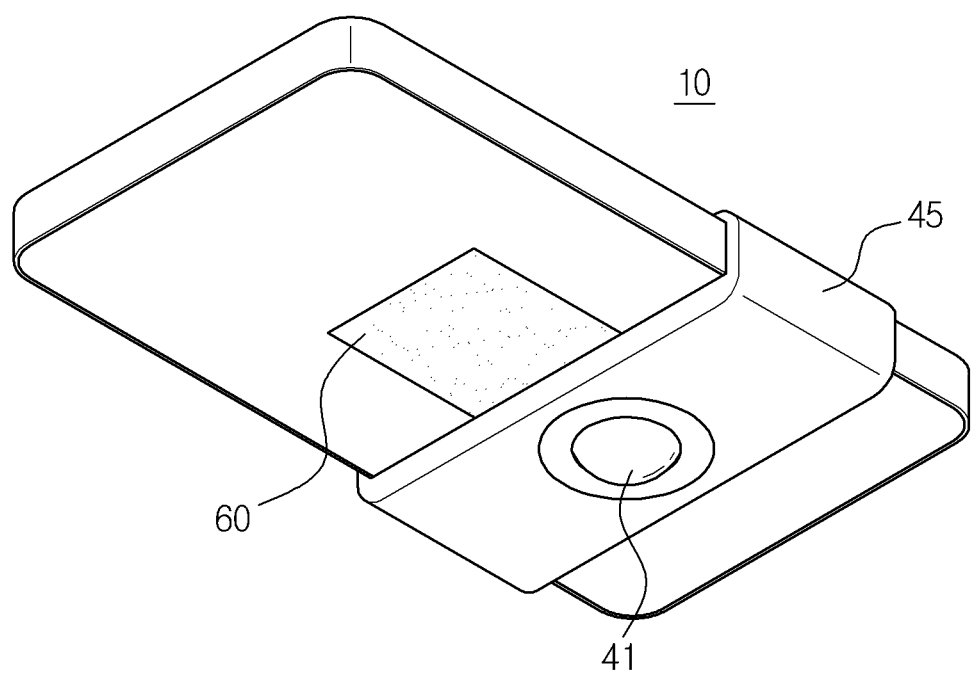
FIG. 10 is a rear perspective view illustrating a configuration of a portable ultrasonic diagnostic apparatus according to a further embodiment of the present disclosure.

FIG. 10 is a rear perspective view illustrating a configuration of a portable ultrasonic diagnostic apparatus according to a further embodiment of the present disclosure.

In FIG. 10, the portable ultrasonic diagnostic apparatus 10 is configured such that the touch panel 60 is attached to a rear surface of the main body 20 and the separable member 45 provided with the track ball 41 is mounted to the rear surface of the main body 10 to which the touch panel 20 has been attached.

Accordingly, by coupling the separable member 45 provided with the track ball 41 to a desired position of the rear surface of the main body 20, the user can operate the track ball 41 while gripping the main body 20 with one hand regardless of the size of the user's hand and can select user command information, such as mode change, content change, screen pause and the like foe an ultrasonic image to be displayed via the touch panel 60.

As is apparent from the above description, the embodiments of the present disclosure provide a portable ultrasonic diagnostic apparatus, which includes an input device provided at a rear surface of a main body thereof to allow a user to operate the portable ultrasonic diagnostic apparatus with one hand that is gripping the main body. Accordingly, a separate platform or cart required to place the portable ultrasonic diagnostic apparatus thereon may be unnecessary, which reduces an equipment price and allows the user to conveniently grip the portable ultrasonic diagnostic apparatus.

Further, as the input device to receive a user command is provided at the rear surface of the main body, the size of the portable ultrasonic diagnostic apparatus may be minimized and an ultrasonic image may be displayed on the entire screen, which expands a visual field of the ultrasonic image, resulting in enhanced user satisfaction.

Although the embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A portable ultrasonic diagnostic apparatus comprising:
    an ultrasonic probe;
    a main body having a size and weight to be gripped by one hand of a user and including a display provided on a front surface of the main body; and an input device provided at a rear surface of the main body to receive and change user command information by use of a finger of the user's hand which is positioned on the rear surface of the main body when the user grips the main body, wherein the display is configured to receive the user command information from the input device and to display an ultrasonic image based on the user command information, and wherein the input device is configured to receive a freeze command to pause the ultrasonic image.

2. The apparatus according to claim 1, wherein the main body further includes:
   a beam former configured to produce frame data by focusing ultrasonic signals received from the ultrasonic probe;
   an ultrasonic data producer configured to produce ultrasonic data via digital signal processing of the frame data;
   an ultrasonic image producer configured to produce an ultrasonic image using the ultrasonic data; and
   a controller configured to control display of the ultrasonic image and a user interface according to the user command information.

3. The apparatus according to claim 2, wherein the controller is configured to control a provision of the user interface and optimization of the ultrasonic image according to the user command information.

4. The apparatus according to claim 1, wherein the input device includes a track ball.

5. The apparatus according to claim 4, wherein the track ball is configured to input the user command information corresponding to a request and selection of a user interface.

6. The apparatus according to claim 4, wherein the track ball is configured to input the user command information corresponding to a setting request of a region of interest included in an ultrasonic image, a size adjusting request of the region of interest, and a movement request of the region of interest.

7. The apparatus according to claim 4, wherein the input device includes at least one button provided at upper and lower sides or left and right sides of the track ball.

8. The apparatus according to claim 7, wherein the at least one button includes a first button to change a display mode of an ultrasonic image or a second button to pause a display screen of the ultrasonic image.

9. The apparatus according to claim 4, wherein the input device includes a touch panel.

10. The apparatus according to claim 1, wherein the input device includes an image mode change button to change an ultrasonic image mode.

11. The apparatus according to claim 1, wherein the input device is separably coupled to the main body.

12. The portable ultrasonic diagnostic apparatus of claim 1, wherein the input device is provided on a separable member that is separately coupled to the main body, and a position of the separable member is changed in consideration of a size of a hand of the user.

13. A method of producing an ultrasonic image using a portable ultrasonic diagnostic apparatus comprising:
   an ultrasonic probe;
   a main body having a size and weight to be gripped by one hand of a user and including a display provided on a front surface of the main body; and
   an input device provided at a rear surface of the main body to receive and change user command information by use of a finger of the user's hand which is positioned on the rear surface of the main body when the user grips the main body, wherein the method comprises the steps of:
   moving the ultrasonic probe in contact with a surface of an object,
   sending ultrasonic signals from the object surface,
   receiving reflected ultrasonic signals from the object,
   converting the received ultrasonic signals into electrical signals,
   controlling display of the ultrasonic image on said display according to the user command information, and
   pausing the ultrasonic image when a freeze command is received by the input device.

14. The method of claim 13, further comprising the steps of:
   producing frame data by focusing ultrasonic signals received from the ultrasonic probe;
   producing ultrasonic data via digital signal processing of the frame data;
   producing the ultrasonic image using the ultrasonic data; and
   controlling display of the ultrasonic image and a user interface according to the user command information.

15. The method of claim 14, wherein the producing the ultrasonic image comprises producing the ultrasonic image including at least one from the group consisting of a Brightness (B) mode image, a Color (C) mode image, a Pulsed-Wave (PW) mode image, a Motion (M) mode image, a Doppler (D) mode image, and a Continuous Wave (CW) mode image.

* * * * *